(12) United States Patent
Hemanthkumar

(10) Patent No.: US 11,124,393 B2
(45) Date of Patent: Sep. 21, 2021

(54) RADIOTHERAPY FACILITY LIFTING APPARATUS

(71) Applicant: Elekta AB (Publ), Stockholm (SE)

(72) Inventor: Sujitkumar Hemanthkumar, West Sussex (GB)

(73) Assignee: Elekta AB (Publ), Stockholm (SE)

( * ) Notice: Subject to any disclaimer, the term of this patent is extended or adjusted under 35 U.S.C. 154(b) by 110 days.

(21) Appl. No.: 16/146,248

(22) Filed: Sep. 28, 2018

(65) Prior Publication Data
US 2019/0100415 A1    Apr. 4, 2019

(30) Foreign Application Priority Data
Sep. 29, 2017    (GB) .................................... 1715858

(51) Int. Cl.
| | |
|---|---|
| *B66C 23/24* | (2006.01) |
| *B66C 23/62* | (2006.01) |
| *B66C 23/68* | (2006.01) |
| *B66C 23/20* | (2006.01) |
| *A61N 5/10* | (2006.01) |
| *G01R 33/28* | (2006.01) |

(52) U.S. Cl.
CPC ............ *B66C 23/24* (2013.01); *B66C 23/208* (2013.01); *B66C 23/62* (2013.01); *B66C 23/68* (2013.01); *A61N 2005/1055* (2013.01); *G01R 33/28* (2013.01)

(58) Field of Classification Search
CPC ......... B66C 23/04; B66C 23/20; B66C 23/24; B66C 23/208; B66C 23/62; B66C 23/64; B66C 23/68; E04H 3/08; G01R 33/28
See application file for complete search history.

(56) References Cited

U.S. PATENT DOCUMENTS

| | | | | |
|---|---|---|---|---|
| 1,540,630 A | * | 6/1925 | Jenks .................... | B66C 23/208 |
| | | | | 212/223 |
| 1,561,226 A | * | 11/1925 | Geoghegan ........... | B66C 23/208 |
| | | | | 212/253 |

(Continued)

FOREIGN PATENT DOCUMENTS

| | | |
|---|---|---|
| CN | 2328640 Y | 7/1999 |
| CN | 104533109 A | 4/2015 |

(Continued)

OTHER PUBLICATIONS

Machine Translation for DE 370575 (Year: 1923).*

(Continued)

*Primary Examiner* — Michael R Mansen
*Assistant Examiner* — Juan J Campos, Jr.
(74) *Attorney, Agent, or Firm* — Finnegan, Henderson, Farabow, Garrett & Dunner LLP

(57) ABSTRACT

A lifting apparatus for a facility combining magnetic resonance imaging apparatus and radiotherapy apparatus inside a purpose-built structure having a fixed wall, the lifting apparatus comprising a wall-mounted articulating jib crane which is selectively moveable between a stowed state and a free state in which it is operable as a crane, in which substantially all of the load-bearing parts of the crane are made of non-ferromagnetic metal, and in which guides are mounted to the wall to receive and to releasably hold the crane in a fixed position relative to the wall when the crane is in the stowed state.

11 Claims, 6 Drawing Sheets

(56) References Cited

U.S. PATENT DOCUMENTS

| | | | | |
|---|---|---|---|---|
| 3,192,041 A | * | 6/1965 | Kanter | .................. C22C 38/001 |
| | | | | 420/59 |
| 5,232,192 A | * | 8/1993 | Akutagawa | ........ B23K 37/0211 |
| | | | | 248/283.1 |
| 9,630,816 B1 | | 4/2017 | Napieralski | |
| 2008/0053750 A1 | * | 3/2008 | Tseng | ........................ E04G 3/30 |
| | | | | 182/82 |

FOREIGN PATENT DOCUMENTS

| | | | | |
|---|---|---|---|---|
| CN | 205367524 U | | 7/2016 | |
| DE | 370575 C | * | 3/1923 | ............. B66C 23/24 |
| DE | 440488 C | * | 2/1927 | ............. B66C 23/24 |
| DE | 4000288 A1 | | 7/1991 | |
| DE | 102004043575 A1 | | 3/2006 | |
| JP | 2013124162 A | * | 6/2013 | ............. B66C 23/20 |
| WO | WO 01/24972 A2 | | 4/2001 | |

OTHER PUBLICATIONS

Machine Translation for DE 440488 (Year: 1927).*
Machine Translation for JP 2013124162 (Year: 2013).*
Search Report in corresponding GB Application No. 1715858.5 dated Mar. 14, 2018 (4 pages).

* cited by examiner

RADIOTHERAPY FACILITY LIFTING APPARATUS

CROSS-REFERENCE TO RELATED PATENT APPLICATIONS

This application claims the benefit and priority of prior United Kingdom Patent Application No. GB1715858.5, filed on Sep. 29, 2017, the entire contents of which are incorporated by reference herein.

FIELD OF THE INVENTION

The present invention relates to lifting apparatus for radiotherapy facilities, particularly large, shielded radiotherapy suites, particularly but not exclusively facilities which combine magnetic resonance imaging systems and radiotherapy systems.

BACKGROUND ART

There are many designs of radiotherapy apparatus, but an increasingly prevalent type utilises a rotatable radiation source such as a linear accelerator, mounted so as to be rotatable around a patient support on which a patient can be placed for treatment, in combination with a magnetic resonance imaging (MRI) system (the combination is known as a MRI/Linear Accelerator, or MRL); the patient support is usually movable into and out of the MRI system. Such an MRL is normally provided in a bespoke facility, or suite, which is constructed within a substantial structure to provide sufficient shielding for the MRI system to operate without external influences adversely affecting imaging quality, and to contain the radiation used in therapy. These suites are usually divided into a treatment space which the patient inhabits (a space in which the patient receives therapy and through which the patient enters and leaves the suite) and a separate maintenance space which is used for adjusting, repairing, maintaining and modifying the MRL equipment. The imaging and radiotherapy systems are located in the maintenance space, and they provide a volume in which imaging and therapy takes place which is in the treatment space; this volume is usually in the form of a horizontal, cylindrical space into which the patient support can place the patient, whilst imaging and therapy systems rotate around the axis of the cylinder so as to provide images and/or radiotherapy from any angle. In one MRL design, the MRI system is in the form of a drum comprising two coaxial cylinders which are spaced a short axial distance from each other, and the linear accelerator (or other radiotherapy apparatus, and/or other imaging apparatus such as a computational tomography (CT) scanner) is arranged to rotate about the axis in the axial space. The walls of the treatment space are usually designed to enclose the part of the drum in which the patient is placed, so as to screen the imaging and therapy apparatus from the patient's view, and are usually contiguous with the walls, floor and/or ceiling of the room which the patient occupies, so as to separate the treatment space from the maintenance space.

It is expensive to construct new purpose-built facilities, and not all hospitals and healthcare facilities have land available to build on. Therefore it is preferable to re-use and re-fit existing space and facilities where possible. As the electromagnetic and radiation shielding required can be expensive, there is also a desire to restrict the overall size as far as is practicable to minimise cost. It is non-trivial design challenge to present the patient with an open and spacious treatment environment, and the service or maintenance engineer with enough space to work on the machine, and yet still fit the facility into an existing radiotherapy bunker.

Many of the tasks which need to be undertaken on the radiotherapy apparatus in the maintenance space require some sort of lifting apparatus, because many of the constituent parts of the imaging and radiotherapy systems which require adjustment or removal and replacement are large, bulky and/or too heavy to be lifted and accurately maneuvered manually in the limited space available. For example, a multi-leaf collimator which is used to collimate the radiation beam emitted by a linear accelerator could weigh about 250 kg and the beam generation module of the linear accelerator could weigh about 1 tonne and is typically about 2 m long. Ideally a lifting apparatus such as a crane is required, but the space limitations mean that it is very difficult to maneuver a crane within the treatment space, particularly when it is carrying a load. Also, cranes are normally metallic, and the presence of a significant metal structure in close proximity to an MRI system is undesirable due to three main factors: the metal of the crane interferes with the sensitivity of the MRI system because it distorts the electro-magnetic field by which an MRI system operates, and this can adversely affect imaging quality; if the crane is moved even slightly in the maintenance space, it will distort the electro-magnetic field in a different way, so that successive images are not accurately comparable, which significantly and undesirably affect the accuracy with which radiotherapy can be applied, and the substantial magnetic fields generated by the MRI system (particularly when it is in operation, but also to an extent when it is "dormant", between patients) can cause the metallic crane to move, thus adding to the first two factors. Accordingly it is common to provide a lifting apparatus which can be removed from the treatment space when it is not required. This is however very much a sub-optimal solution, because either a large crane has to be manhandled in and out of the treatment space, through what is usually quite a restricted access route, or the crane has to be brought into the treatment space in pieces and assembled before it can be used, and then disassembled and removed before the imaging system can be used. These are all time-consuming processes, and the expense of such facilities means that great efforts are taken to ensure they are in use for the maximum time possible, so adding to maintenance time the time necessary to prepare and remove a crane for necessary maintenance work seriously detracts from the cost-effective use of the facility.

Other factors also affect the operation of any kind of crane within the limited space available in the maintenance space. For example, the relatively short axial space between the two drums of the MRI system limits the movement of a lifting apparatus: it may be relatively easy to move the longitudinal arm of a crane into this space provided that movement is limited to a direction perpendicular or very close to the axis, but there may be very little freedom for this arm to twist within this space (i.e. for the arm to be angled relative to the axis in this space), and there may be insufficient room between the walls of the treatment space and the exterior of the MRI system for the longitudinal arm of a crane to be maneuvered into the axial space without great difficulty. The height of the ceiling or the position of the shielding may prevent a crane from being able to pass over the gantry, making it difficult to access some components of the machine. The region between the walls of the treatment space and the imaging and radiotherapy systems may also be crossed by pipes/ductwork and the like which are essential for the operation of the systems but which are an obstacle to the movement or operation of a crane, further complicating maintenance processes.

SUMMARY OF THE INVENTION

The present invention arose from the realisation that the space limitation in the treatment space for moving a crane could be mitigated by utilising a jib of effective variable length. Nevertheless, this did not address the problem of having to move the crane in and out of the treatment space, nor did it address the problem of deploying the crane into the limited room between the walls of the treatment space and the exterior of the MRI system or of deploying the crane into and moving the crane within the relatively short axial space between the two drums of the MRI system.

The present invention therefore provides a lifting apparatus adapted and configured for use in a facility combining magnetic resonance imaging apparatus and radiotherapy apparatus inside a purpose-built structure having a fixed wall, the lifting apparatus comprising a wall-mounted articulating jib crane (that is, a crane with a projecting arm in two or more parts and which has an articulation, or rotary joint, along its length so that the distal arm part can rotate, and/or be folded against the proximal arm part which is mounted to the wall, preferably via a rotatable joint) which is selectively moveable between a stowed state and a free state in which it is operable as a crane, in which substantially all of the load-bearing parts of the crane are made of a non-ferromagnetic metal material, and in which guides are provided adjacent or on the wall to receive and to releasably hold the crane in a fixed position relative to the wall when the crane is in the stowed state.

Such an articulated jib arrangement allows the crane to be operated within the tight confines of the available space between the walls of the treatment space and the exterior of the MRI system whilst being able to avoid ductwork and the like crossing this space, and to be maneuvered into the relatively short axial space between the two drums of the MRI system when something needs to be lifted or lowered in this region. In between lifting operations, the jib of the crane can be moved into the stowed position, which is preferably flat against the wall, and held there in a reliably repeatable and accurately known position—which means that although the crane may create some distortion of the MRI magnetic field, it does so in a reliably constant manner, so the effects of the distortion on the imaging can be determined once and then compensated for by adjusting the imaging system. The load bearing elements of the crane are usually all those elements which can move when the crane is in use, but they may also include some items which are not easily commercially available in non-ferromagnetic material, such as bearings. Ensuring that the crane consists of a high proportion of non-ferromagnetic material minimises the distortion the crane creates in the MRI imaging field by remaining in the treatment space when the MRI system is in use, whilst also reducing the tendency of that field to move the crane from its stowed position—which in turn means that the guides do not need to withstand a large force, and so can be small, light and relatively inexpensive. The guides could be mounted to the wall. The joint which is mounted to the wall allowing the crane to rotate, preferably about a vertical axis, relative to the wall could be of magnetic material, since it will largely be rotationally symmetrical, so that its effect on the MRI magnetic field would be constant whatever its rotational position, but because it would have a relatively large effect on the field we prefer that this joint also be non-ferromagnetic. The non-ferromagnetic material is preferably a metal alloy (because the manufacturers of cranes are accustomed to manufacture from such materials, and cranes made of such materials are less expensive and more robust than ones made of other materials, such as plastics or composites). We prefer to make the crane from an austenitic stainless steel. It is not the case that such stainless steel is wholly non-magnetic. As is known in the art, the degree of magnetic response or magnetic permeability is derived from the microstructure of the steel. A totally non-magnetic material has a relative magnetic permeability of 1. Austenitic structures are totally non-magnetic and so a 100% austenitic stainless steel would have a permeability of 1, but in practice this is not achieved. There is always a small amount of ferrite and/or martensite in the steel and so permeability values are always above 1. Typical magnetic permeability values for standard austenitic stainless steels are usually in the order of 1.05-1.1, but in austenitic steels for MRI purposes it can be as low as 1.004. The term "non-ferromagnetic" is used herein to denote any metal material having a magnetic permeability within the range 1.000-1.15, and so encompasses materials other than stainless steel; it should be construed as excluding any paramagnetic material which exhibits appreciable magnetic attraction (or repulsion) when under the high magnetic fields typical in a MRI facility, such as aluminium or aluminium alloy. It is preferred to use a metallic non-ferromagnetic material rather than, say, plastics or composite material because the former is less expensive and its long term durability in a high radiation environment is better known.

There may be a wall-mounted slide or rail to which the crane is mounted so as to be movable along the wall when in the free state, and in which substantially all of the moveable parts of the crane are made of non-ferromagnetic material. Such a mounting for the crane allows the crane a greater range of movement within the treatment space, preferably in the horizontal plane, and can provide a stowing position for the crane which as far from the MRI system as the treatment space constraints permit; this reduces the distorting effect of the moveable parts of the crane on the MRI magnetic field. The slide is wall mounted (i.e. fixed), and so need not necessarily be of non-ferromagnetic material, as it would have a constant distorting effect on the magnetic field. There may be a mechanism adapted selectively to releasably secure the crane relative to the slide, such as when the crane is moved to the stowed state. This mechanism may also be capable of securing the crane in a particular horizontal position during operation of the crane, or there may be a second mechanism for this.

There may be a single articulation in the crane, with the jib comprising two longitudinal arms extending therefrom. We have found that such an arrangement provides an optimal compromise between the need to be able to lift and lower items with the crane and to be able to maneuver the laden or unladen crane in the cramped treatment space, and into the axial space between the two drums of the MRI system, whilst avoiding pipes and ducting which cross the treatment space, and the need to keep the crane relatively small and light. The articulation adds mass to the jib, and the greater the mass of the jib the more massive the crane has to be to support a load, so an arrangement with more than one articulation would be feasible but would be undesirable from the weight and size perspectives. Similarly, the jib could be an extending (e.g. telescopic) jib, however this would also tend to add mass and complexity to what can be a relatively simple design.

There may be a locking mechanism acting at the articulation and adapted to hold the arms fixed relative to one another; this could be in the form of a pin which can engage in one of a number of holes formed in a plate so that the distal arm can be locked at one of a number of angles relative to the proximal arm. The arms could be parallel so that the jib is at its maximum length (either for operating, to give the crane its maximum reach, or for stowing), or so that the distal arm is folded against the proximal arm (for stowing the crane). The arms can be of substantially equal length, or the distal arm can be slightly longer than the proximal arm (which is usually more massive and stronger than the distal arm). There may be a further mechanism mounted to the wall to receive and to releasably hold the articulation in a fixed position relative to the wall when the crane is in the stowed state.

For simplicity there may be a chain hoist at the end of the jib for lifting and lowering items in the treatment space, and this hoist is preferably distant from the wall-mounting of the jib when the crane is in the free state. This is a reliable means of lifting heavy weights, and of course it should be mounted at the distal end of the jib. Because the hoist may contain magnetic elements whose position can move between operations, locating the hoist at the distal end of the jib allows these elements to be distanced as far as possible from the MRI system when the crane is stowed, so reducing the absolute distortion and the unreliable distortion of the magnetic field the elements produce. The hoist could be removably attached to the crane, and the hoist could be a conventional integrated differential pulley system, which is a well-known arrangement for providing a mechanical advantage in lifting weights. There may be a rotating gantry for mounting a radiotherapy apparatus, allowing the gantry to be rotated to locate any part of the radiotherapy apparatus to be positioned under the lifting end of the crane.

In a further aspect, the present invention provides a facility combining magnetic resonance imaging apparatus and radiotherapy apparatus inside a purpose-built structure and comprising a lifting apparatus as described above. In order to solve the problem of being able to maneuver the crane in the usually confined space between the wall and roof of the facility and the MRL so as to lift elements of the MRL, for installation, maintenance or replacement purposes we have found it advantageous, where the magnetic resonance imaging apparatus and the radiotherapy apparatus have a common axis, and where the articulating jib has an end which, in use, is configured to lift, lower or support a load, for the dimensions of the articulating jib to be such that when the jib is fully extended in the free state such that the said end of the jib is at its furthest extent from the wall the said end does not extend as far as the axis.

The invention also provides a method of use of a crane in a facility combining magnetic resonance imaging apparatus and a rotary radiotherapy apparatus, the method comprising extending the jib in the free state and rotating the radiotherapy apparatus so as to bring a part of the radiotherapy apparatus into the vicinity of the end of the jib. This provides a crane which works in co-operation with the rotating gantry of the radiotherapy apparatus to allow lifting access to any part of the gantry, even though the crane cannot reach all the way around the gantry. This allows the crane according to the invention to be fitted into and to operate effectively around a MRL within the confines of a regular sized bunker.

BRIEF DESCRIPTION OF THE DRAWINGS

The invention will now be described by way of example and with reference to the accompanying figures, in which.

DETAILED DESCRIPTION OF THE EMBODIMENTS

Figure 1A:
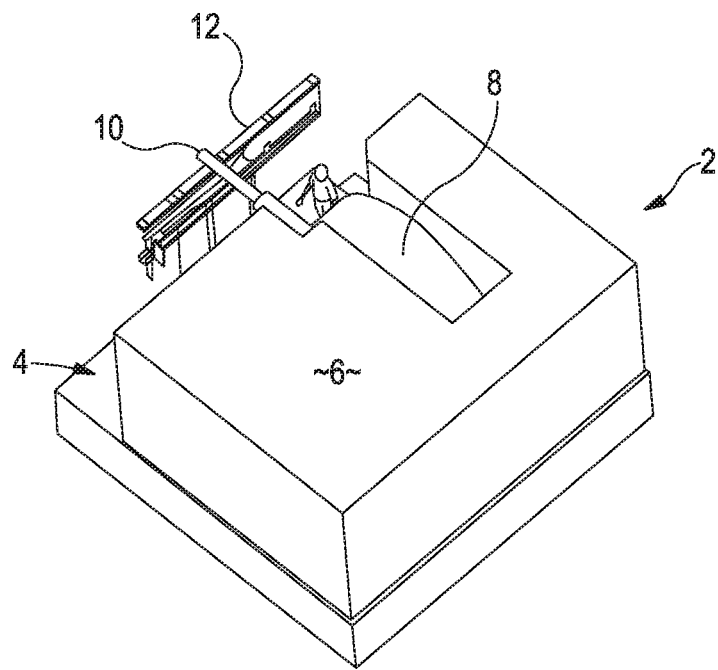
FIGS. 1a, 1b and 1c are schematic perspective, front elevation and plan views of a radiotherapy facility having a lifting apparatus in accordance with the present invention, showing the lifting apparatus in a first configuration.
Figure 1B:
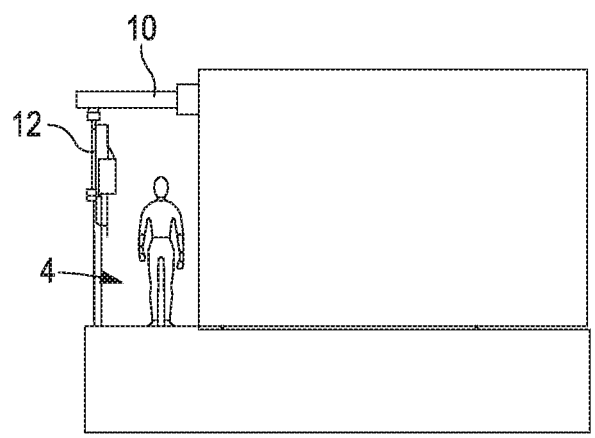
Figure 1C:
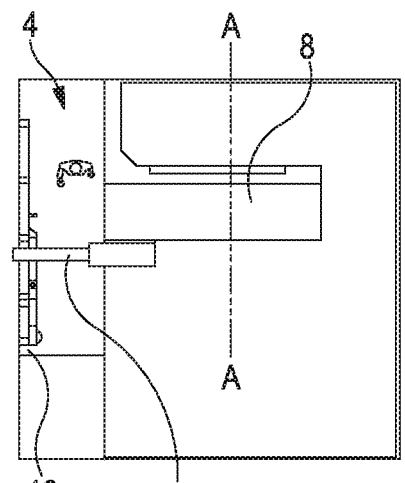

FIGS. 1a, 1b and 1c show schematically an MRL facility 2 with outer walls removed so that the maintenance space 4 is visible (a human figure is shown in this space to give an indication of scale). An enclosure 6 surrounds the treatment space, where a patient receives radiotherapy; this enclosure is shown as a box-like structure, which has a break in the box shape for maintenance access to the MRL (the rotating gantry part of which can be seen, indicated by the reference numeral 8, shown as a cylindrical shape; this break corresponds to the short axial space along the axis AA of the MRI system, in which space the radiation source and any other imaging system (i.e. other than the MRI, but not shown) is able to rotate with the gantry 8 about the patient and the axis AA). A duct 10 crosses the treatment space between the MRL and the outer wall (not shown) of the maintenance space 4 for carrying coolant to and from the MRL, and electrical cables for transmitting power and control signals to the MRL and imagery signals from the MRL to a remote control room. A wall-mounted crane 12 (described in more detail below) is provided in the maintenance space 4, and is shown flat against the outer wall of the maintenance space 4 (i.e. with the jib fully extended and parallel to the wall).

Figure 2:
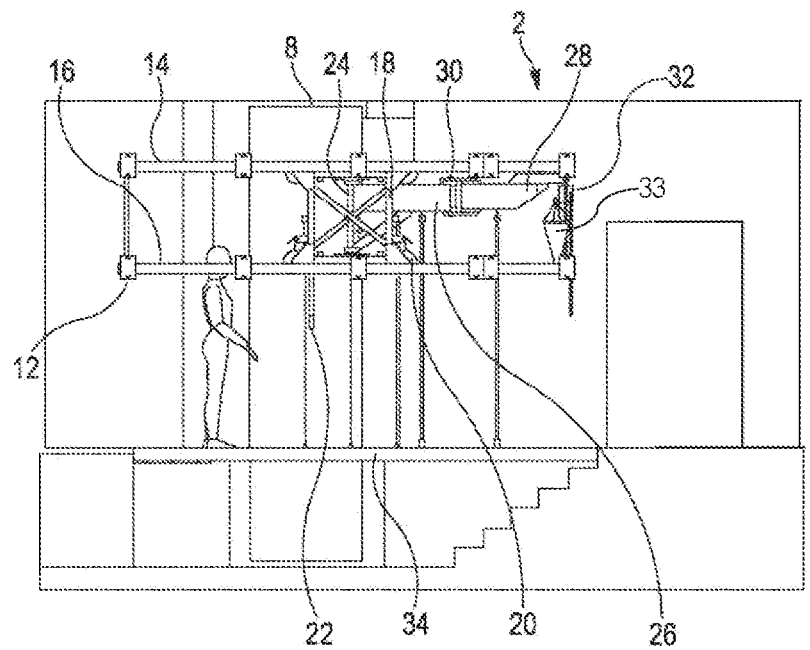
FIG. 2 is a schematic side elevation of the facility of FIG. 1.
Figure 3:
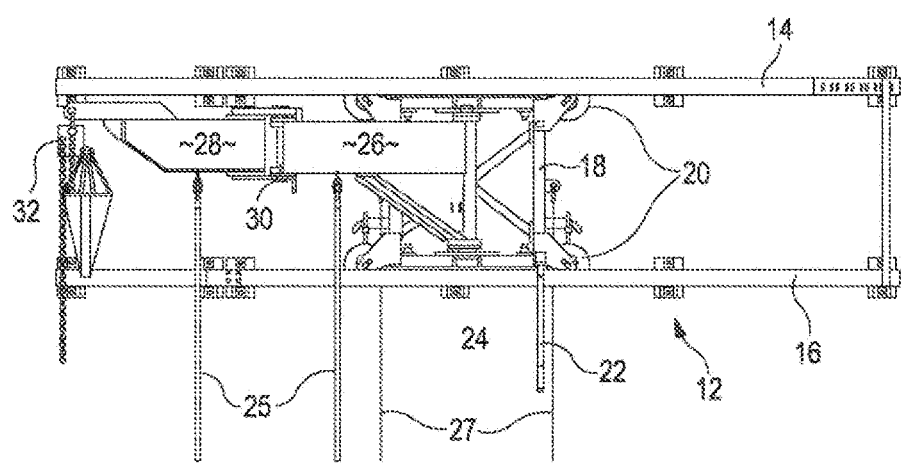
FIG. 3 is an elevation view of the crane in FIG. 2 seen from the other side.

FIG. 2 shows a side elevation of the facility 2 of FIG. 1 (with the ductwork 10 omitted for clarity) and the crane 12 in more detail from the rear. FIG. 3 shows the crane 12 from the other side. Crane 12 is a sliding, wall-mounted articulated jib crane. This crane comprises horizontal upper and lower rails 14, 16 which are fixed to the wall of the maintenance space along which a frame 18 carrying the articulated jib can run freely on four selectably lockable wheels 20; a handle 22 and flexible straps 27 are provided for moving the frame 18 and jib along the rails 14, 16. The articulated jib is mounted to the frame 18 so as to be rotatable in the horizontal plane around a vertical pivot joint 24, and consists of inner and outer arms 26, 28; the outer arm 28 is mounted to the inner arm 26 so that it can rotate in the horizontal plane about another vertical pivot joint 30 (and the jib can "articulate"). The pivot joint 30 is selectively lockable, so that the outer arm 28 can be held in a fixed angular position relative to the inner arm 26; similarly, the pivot joint 24 is also selectively lockable, so that the inner arm 28 can be held in a fixed angular position relative to the frame 18, either at a fixed number of different angles or at any angle. At the distal end of the jib, furthest from the pivot joint 24, a chain hoist 32 (which may include a pulley system 33) is releasably attached. It will be noted in FIG. 2 that the MRL 8 extends below the floor level of the maintenance space; a removable floor 34 is provided to allow access to the lower part of the MRL 8 via steps going down to a lower level floor underneath the gantry 8, for maintenance or other purposes. In FIGS. 2 and 3 the crane 2 is again shown with the jib fully extended and flat against the wall, in the stowed position the jib could be held flat against the wall like this, or with outer arm 28 folded alongside inner arm 26, by releasable locking guides 36 (shown in FIG. 5b). Flexible straps 25 hang down from the jib arms 26, 28, and help an operator to move the jib arms. Additional straps 27 hang down from the frame 18.

Figure 4A:
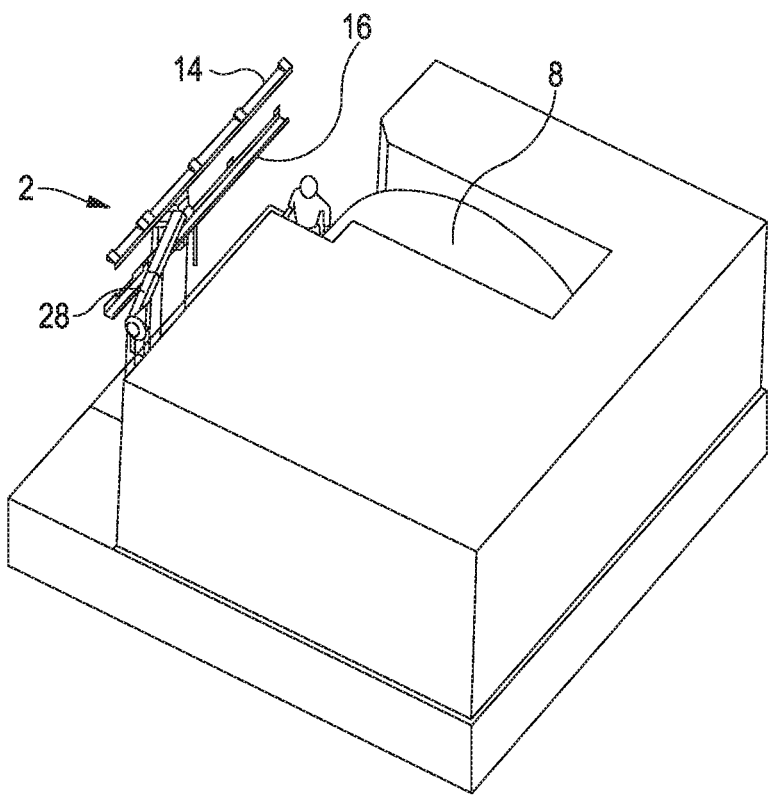
FIGS. 4a and 4b are schematic perspective and plan views of the facility of FIG. 1 showing the lifting apparatus in a second configuration.
Figure 4B:
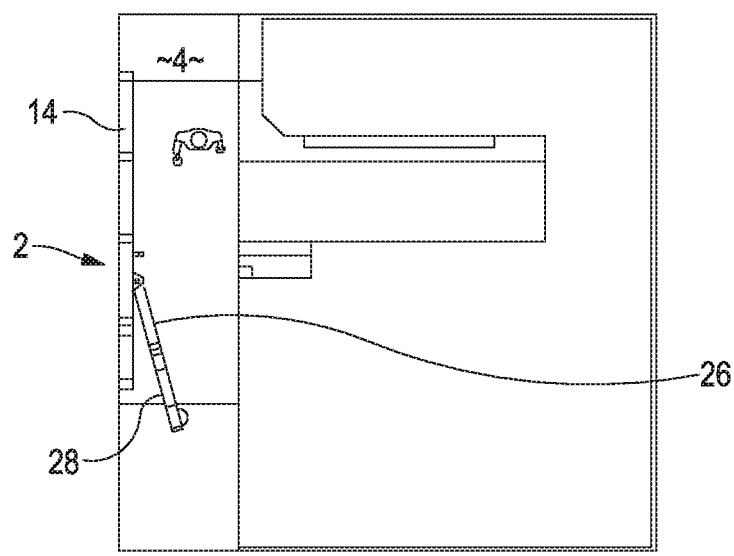
Figure 5:
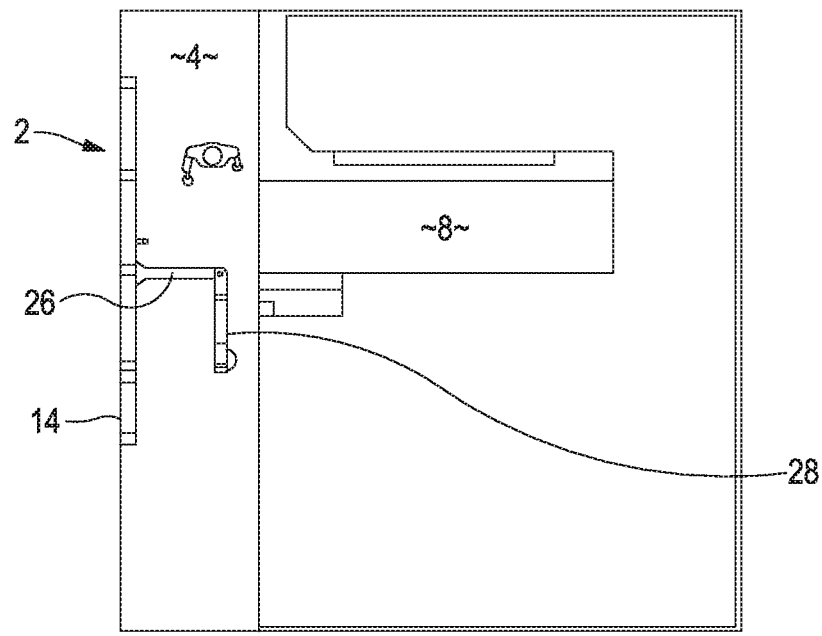
FIG. 5 is a schematic plan view of the facility of FIG. 1 showing the lifting apparatus in a third configuration.

In FIGS. 4a and 4b the outer and inner arms 26, 28 of the jib are fully extended, i.e. locked at pivot joint 30 so as to be parallel but the jib as a whole is rotated approximately 30° about pivot joint 24 so that the distal end of outer arm 28 and chain hoist 32 are spaced away from the wall of the maintenance space. In FIG. 5 the inner arm 26 is locked at pivot joint 24 so as to be perpendicular to the wall of the maintenance space and the outer arm 28 is locked at pivot joint 30 so as to be perpendicular to inner arm 26, and in FIGS. 6a to 6c the inner arm 26 is locked at pivot joint 24 so as to be perpendicular to the wall of the maintenance space and the outer arm 28 is locked at pivot joint 30 so as to be parallel to inner arm 26, so that the distal end of the jib, and the chain hoist 32, is located towards the centreline of the MRL 8. It will be understand that by combining sliding the frame 18 along the rails 14, 16, rotating inner arm 26 about pivot joint 24 and rotating outer arm 28 about pivot joint 30, the jib can be manipulated and maneuvered so as to be operable (used for raising or lowering heavy items) in virtually any position within the maintenance space. The chain hoist 32 shown is manually operated, but it could be powered. The crane has to be load tested at regular intervals to ensure that it is safe to use, and this is usually done with the crane 2 in what is structurally its weakest configuration, which is as shown in FIG. 5; conveniently a fixed eye 38 (shown in FIG. 6b) is embedded in the floor of the maintenance space for this purpose so that the chain hoist 32 can be attached to this eye 38 via a load cell to load test the crane 2.

As mentioned above, the crane 2 is stowed away when the MRL is in use; in the stowed position, the jib is put in the configuration of FIG. 1 (or the outer arm 28 is rotated fully about pivot joint 30 so as to lie alongside inner arm 26) and the frame 18 is moved along rails 14, 16 so that the jib is in the correct position to engage with releasable locking guides 36. The guides 36, the pivot joints 24, 30 and the wheels 20 are then locked so that all of the moveable parts of the crane 2 are fixed in a known position. As explained above, this ensures that the distortion in the magnetic operating field of the MRI caused by the crane is always the same, and that the moveable parts are held securely so as not to be moved by the magnetic field when the MRL 8 is in use. The distortion is minimised by making the crane, or at least its moveable parts, of non-ferromagnetic material, such as austenitic stainless steel, and by positioning the stowed location so that when stowed the jib is distant from the MRI system. Bringing the stowed crane 2 into use is a simple matter of unlocking the guides 36, the pivot joints 24, 30 and the wheels 20, moving and manipulating the crane so that the distal end of the jib is in the desired position, and re-locking one or more of the guides 36, the pivot joints 24, 30 and the wheels 20.

Figure 7:
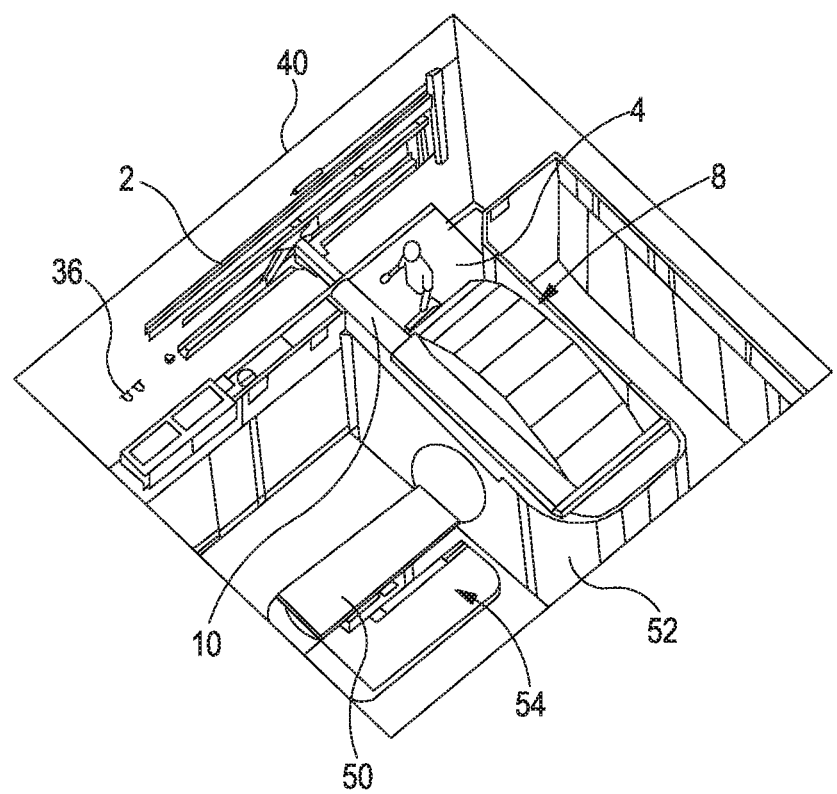
FIG. 7 is a schematic perspective view of the facility of FIG. 1 showing the lifting apparatus in the fourth configuration.

FIG. 7 shows a few more features of the radiotherapy facility, such as the enclosure wall 40 of the maintenance space 4 to which the crane 2 is mounted, the patient support 50, on which the patient lies before being moved axially into the MRL 8, and the walls 52 which separate the treatment space 54 from the maintenance space 4 and enclose the part of the drum in which the patient is placed, so as to screen the imaging and therapy apparatus from the patient's view.

Figure 6A:
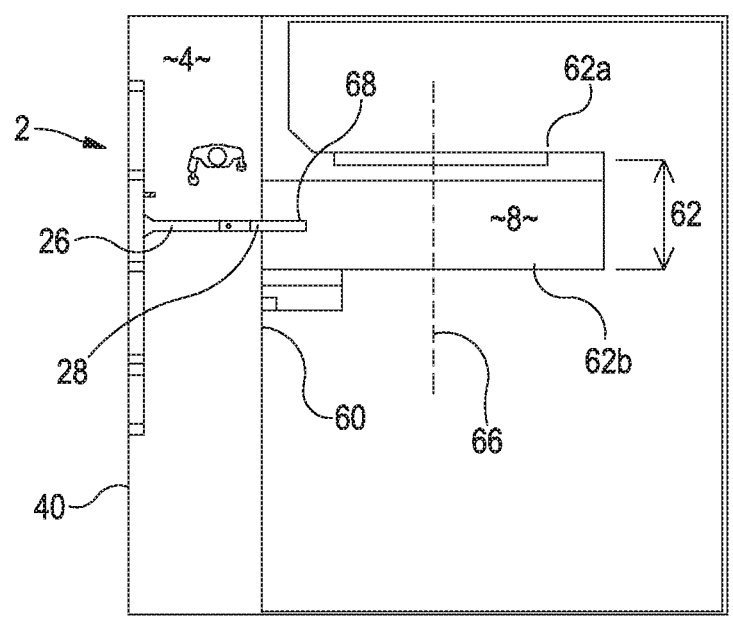
FIGS. 6a and 6b are schematic plan and side elevation views of the facility of FIG. 1 showing the lifting apparatus in a fourth configuration.

Turning again to FIGS. 6a and 6b, we will explain how the crane 2 is dimensioned and used in the confined space typically available in a radiotherapy facility. There is often a restricted distance between the inner wall 40 of the facility to which the crane 2 is mounted and the edge 60 of the enclosure wall 52 parallel to the inner wall 40, and the distance 62 between the enclosure wall 52 where it surrounds the MRI apparatus 8 is usually short relative to the radius of the MRI apparatus. There may also be very little vertical distance between the ceiling of the facility (shown generally as 64 in FIG. 6b) and the uppermost point of the MRL 8, so it would not be possible for the jib to extend as far as the axis 66 of the MRL, and even if the jib did extend this far there would be insufficient room for a hoist to lift heavy items; however, the jib can be dimensioned such that when it is fully extended as shown in FIG. 6a its lifting end 68 is somewhat distant from the axis 66 (vertically above the level of the axis 66 and horizontally not extending as far as the axis 66 but so as to be between the axis 66 and the outer circumference of the MRI 8 in the horizontal plane, as shown in FIG. 6a). Such an arrangement allows the outer and inner arms 26, 28 of the jib to be maneuvered in the confined space, and extended to the position shown in FIG. 6a. In order to lift elements of the MRI 8, for installation, maintenance or repair purposes, the MRI 8 is rotated about the axis 66 to bring the part of the MRI which is to be lifted into a position beneath the end 68 of the fully-extended jib.

Figure 6B:
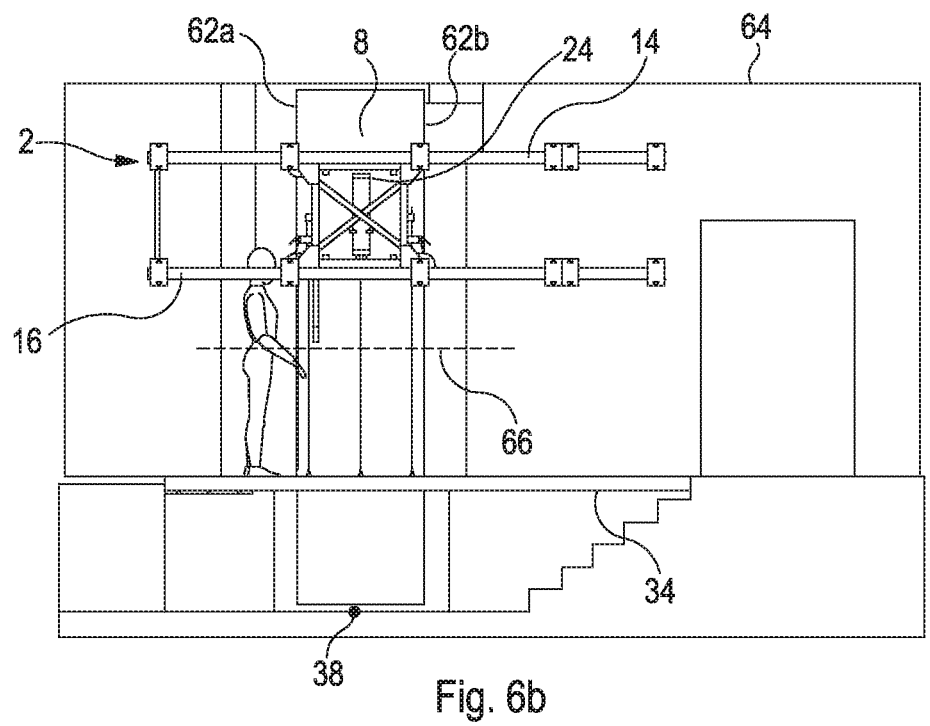
Figure 8:
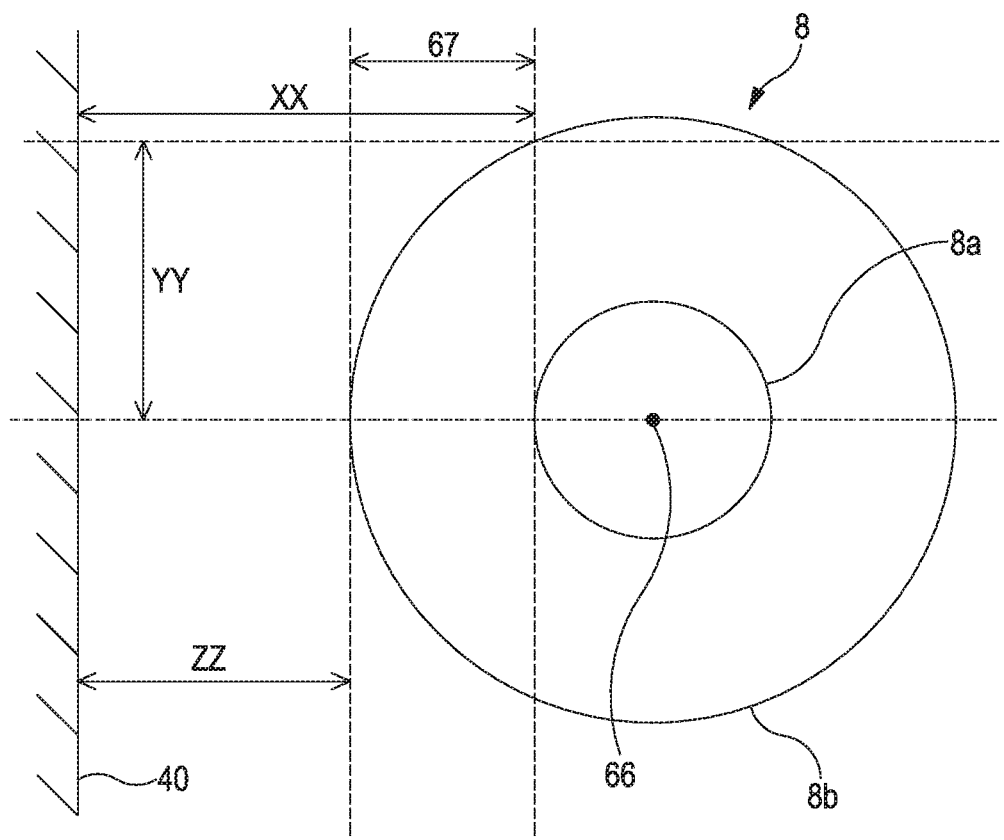
FIG. 8 is a schematic front elevation of the facility showing the relationship between a gantry and a facility wall.

FIGS. 6a and 6b also illustrate a further advantage of the facility containing the wall-mounted articulated jib crane 2; both Figures show that there is little axial space between the sides 62a, 62b of the rotating gantry 8 and the enclosure wall 52 where it surrounds the rotating gantry 8 (the apparent gap adjacent to side 62a in FIG. 6a is misleading, the rotating gantry 8 has an axial length 62 which is only very slightly less than the distance between the opposed sides of the enclosure wall 52 where it surrounds the rotating gantry 8). FIG. 6b shows that there is also very little distance between the floor and ceiling 64 of the facility and the upper and lower extremities of the rotating gantry 8. This restriction of space surrounding the gantry 8 is deliberate, as it is usually necessary to fit a gantry having the largest possible diameter within a bunker of fixed dimensions or, when constructing a facility around an MRL it is desirable not to make the facility any larger than necessary so as to limit construction costs and/or to avoid impacting on existing adjacent structures (MRL facilities are often constructed next to existing hospital buildings/facilities and there may be only limited space available between these buildings/facilities). This means that the crane 2 can only access the gantry 8 in the slightly-less than quartile of the circumference of the MRL between the horizontal level of the axis 66 as shown in FIG. 6b and FIG. 8 and a position slightly short of the highest extremity of the gantry 8 as shown by the axis 66 in FIGS. 6a and 8. Provided that the end 68 of the jib is able to extend horizontally over this distance, it does not matter that the crane cannot extend over the entire diameter of the gantry 8 because the gantry 8 can be easily rotated to locate any element on the gantry which has to be lifted by the crane vertically beneath the end 68. It will also be understood that the lengths of the outer and inner arms 26, 28 of the jib are chosen so as to be capable of allowing the end 68 of the jib to be extended horizontally as far as possible towards the axis 66 within the limited distance 62; depending on the distance 62 between the sides 62a, 62b of the gantry 8, on the distance between the inner wall 40 of the facility to which the crane 2 is mounted and the edge 60 of the enclosure wall 52 parallel to the inner wall 40, on the distance between the uppermost edge of the gantry 8 and the ceiling 64, on the diameter of the gantry 8 and on the vertical distance between the top of the crane and the chain hoist (at its minimum length) or the like at the lifting end of the jib, it is relatively easily determined as a matter of geometry how long the jib arms 26, 28 should be, or if more than two jib arms are required, to give the necessary flexibility for the crane to unfold and extend over the gantry in the limited room between the walls and ceiling of the bunker and the gantry, and the narrow "slot" extending radially between the opposed sides of the enclosure wall 52 on either axial side of the gantry. In addition, as shown schematically in FIG. 8, where the gantry 8 includes a cylindrical central bore 8a, co-axial with the axis 66, which is designed to allow a patient to be passed into the radiotherapy equipment, there arises an optimum operational distance 67 along the horizontal level of the axis 66 between the circumference of the bore 8a and the external circumference 8b of the gantry 8 which defines a minimum operation range of the crane necessary for the jib to access all components mounted on the gantry 8. Furthermore, by determining the distance of this minimal operating range 67 of the jib relative to the facility wall 40 (distance ZZ) it is then possible, through basic geometry and knowledge of the outer diameter 8b of the cylindrical gantry 8 to determine a minimum required height (YY) that the jib need be mounted above the axis horizontal level 66 in order to allow access to all components on the gantry 8. In combination with knowledge of the minimum distance ZZ between the outer circumference 8b of the gantry 8 and the facility wall 40 it becomes possible to optimise the bunker facility design process to provide a crane capable of accessing all components on a cylindrical gantry by appropriate variation and specification of the outer and inner arms 26, 28 of the jib and the jib height above the axis level 66. Conversely, extrapolation of the gantry dimensions—and notably the radius of the gantry bore 8a and the radius of the gantry external diameter 8b-coupled with the distance 62 will enable the facility designers to determine minimum jib arm lengths necessary to identify a minimum distance ZZ between the facility wall and gantry.

Accordingly design of the crane can be included in the process of designing the overall facility, and computer aided modelling can be used to ensure that the crane can be used to lift any part of the apparatus mounted to the gantry, whilst ensuring that the general arrangement is as compact as possible.

It will of course be understood that many variations may be made to the above-described embodiment without departing from the scope of the present invention. For example, the non-ferromagnetic material could be an alloy such as bronze or tin. There may be releasable fixings on the inner and outer arms for holding the inner and outer arms together when the outer arm is folded against the inner arm, with guides being provided on the wall to releasably hold the inner arm in the stowed position against the wall. The outer and inner arms 26, 28 of the jib are shown as being the same length but, depending on the size and shape of the limited space between the walls of the facility and the enclosure wall 52 in which the crane has to be usable, it may aid maneuverability for one of the arms to be longer than the other one.

The invention claimed is:

1. A lifting apparatus configured for use in a facility combining a magnetic resonance imaging apparatus and a radiotherapy apparatus within a facility structure having a first wall, the lifting apparatus comprising:
   an articulating crane which is selectively moveable between a stowed state and a free state, wherein a loadbearing part of the crane is made of non-ferromagnetic metal material and wherein the crane is mountable to the first wall; and
   a plurality of guides mountable to the first wall to receive and to releasably hold the crane in a fixed position relative to the first wall when the crane is in the stowed state; and
   a chain hoist connected to an end of a jib of the crane which, when the crane is in the free state, is distant from the first wall, the chain hoist comprising a pulley system.

2. The lifting apparatus in accordance with claim 1 comprising:
   a slide mountable to the first wall and mountable to the crane, wherein the slide is configured to move along the wall when in the free state.

3. The lifting apparatus in accordance with claim 2, comprising a mechanism configured to releasably secure the crane relative to a rail.

4. The lifting apparatus according to claim 1, wherein the crane has a single articulation and comprises two longitudinal arms extending from the single articulation.

5. The lifting apparatus according to claim 4, further comprising a locking mechanism acting at the single articulation and configured to hold the two longitudinal arms fixed relative to one another.

6. The lifting apparatus according to claim 5, wherein the locking mechanism is configured to hold the two longitudinal arms fixed at one of a plurality of angles relative to one another.

7. The lifting apparatus according to claim 4, wherein the two longitudinal arms are of equal length.

8. The lifting apparatus according to claim 4, wherein a mechanism is mountable to the first wall to receive and to releasably hold the single articulation in a fixed position relative to the first wall when the crane is in the stowed state.

9. A method of using the lifting apparatus according to claim 1, the method comprising:
   extending the jib of the crane in the free state, the jib being connected to a rotating gantry of the radiotherapy apparatus; and
   rotating the rotating gantry in order to bring a part of the radiotherapy apparatus toward the end of the jib.

10. The method of using the lifting apparatus according to claim 9, comprising:
    extending the jib in the free state; and
    rotating the rotating gantry about a common axis of the magnetic resonance imaging apparatus and the radiotherapy apparatus in order to bring a part of the radiotherapy apparatus toward the end of the jib.

11. The lifting apparatus in accordance with claim 1, wherein substantially all moveable parts of the crane are made of a non-ferromagnetic material.

* * * * *

UNITED STATES PATENT AND TRADEMARK OFFICE
CERTIFICATE OF CORRECTION

PATENT NO. : 11,124,393 B2  
APPLICATION NO. : 16/146248  
DATED : September 21, 2021  
INVENTOR(S) : Sujitkumar Hemanthkumar Page 1 of 1

It is certified that error appears in the above-identified patent and that said Letters Patent is hereby corrected as shown below:

On the Title Page

Item (30), "1715858" should read --1715858.5--.

In the Claims

Claim 11, Column 10, Line 64, "wherein substantially all" should read --wherein all--.

Signed and Sealed this  
Second Day of August, 2022

Katherine Kelly Vidal  
*Director of the United States Patent and Trademark Office*